United States Patent [19]

Hubbard

[11] Patent Number: 5,440,942
[45] Date of Patent: Aug. 15, 1995

[54] BIOLOGICAL SAMPLE COLLECTING AND HOLDING DEVICE

[76] Inventor: Stephen H. Hubbard, 1076 Emerson Rd., Park Hills, Ky. 41011

[21] Appl. No.: 191,025

[22] Filed: Feb. 2, 1994

[51] Int. Cl.⁶ .................. G01N 1/08; G01N 1/00; G01N 1/28
[52] U.S. Cl. ................ 73/864.91; 73/863.23; 73/864.44
[58] Field of Search .......... 73/864.91, 864.41, 864.44, 73/864.45, 863.23, 863.24, 863.25

[56] References Cited

U.S. PATENT DOCUMENTS

| | | | |
|---|---|---|---|
| 2,835,246 | 5/1958 | Boettger . | |
| 2,969,168 | 1/1961 | Newby | 222/525 |
| 2,998,902 | 9/1961 | Thomas et al. | 222/525 X |
| 3,032,240 | 5/1962 | Dunklee | 222/525 |
| 3,201,013 | 8/1965 | Porter et al. | 222/559 X |
| 3,203,576 | 8/1965 | Wout et al. | 220/39 |
| 3,518,164 | 6/1970 | Andelin et al. | 195/127 |
| 3,811,326 | 5/1974 | Sokol . | |
| 3,936,373 | 2/1976 | Studer | 435/177 X |
| 3,937,211 | 2/1976 | Merten | 128/765 |
| 4,020,981 | 5/1977 | Nixdorff | 222/525 |
| 4,067,443 | 1/1978 | Greenwald | 206/229 X |
| 4,221,225 | 9/1980 | Sloan | 128/750 |
| 4,288,316 | 9/1981 | Hennessy | 209/17 |
| 4,300,404 | 11/1981 | Mehl et al. | 73/863.52 |
| 4,357,240 | 11/1982 | Mehra et al. | 210/455 |
| 4,559,837 | 12/1985 | Cerqueira | 73/863.23 |
| 4,644,807 | 2/1987 | Mar | 73/864.91 X |
| 4,678,559 | 7/1987 | Szabados | 209/17 |
| 4,973,450 | 11/1990 | Schlüter | 73/863.23 X |
| 4,978,504 | 12/1990 | Nason | 422/61 |
| 4,979,648 | 12/1990 | Montgomery et al. | 222/522 X |
| 5,149,506 | 9/1992 | Skiba et al. | 209/17 X |
| 5,200,153 | 4/1993 | Carr et al. | 73/864.11 X |
| 5,246,669 | 9/1993 | Hayashi | 73/864.41 X |

*Primary Examiner*—Thomas P. Noland
*Attorney, Agent, or Firm*—Wood, Herron & Evans

[57] ABSTRACT

A sample collecting and holding device includes a vial and a cap. The cap includes a central opening which can be closed using a push-pull nozzle. A screen or filter also covers the bottom of this central opening and includes an arm having a sample collecting scoop. This permits the user to collect a sample and place it in the liquid-filled vial. The cap, once screwed onto the vial, seals the vial and permits removal of filtered liquid from the push-pull nozzle.

4 Claims, 1 Drawing Sheet

BIOLOGICAL SAMPLE COLLECTING AND HOLDING DEVICE

BACKGROUND OF THE INVENTION

The testing of biological samples requires collection of the biological sample, some storage, and frequently shipment of the biological sample to a medical laboratory.

Accordingly, it is necessary to provide a collection and shipping container which facilitates collection of the biological sample, along with maintaining it in a sealed container where leakage is absolutely prevented.

There are a number of devices designed to collect fecal samples which incorporate a vial and a collecting scoop. Some of these are disclosed, for example, in Boettger U.S. Pat. No. 2,835,246, Grow et al. U.S. Pat. No. 5,198,365, and Skiba et al. U.S. Pat. No. 5,149,506. Particularly with fecal samples, it is frequently necessary to filter or screen the sample after it has been dispersed in a liquid medium. Various devices designed for this are disclosed, for example, in Mehra et al. U.S. Pat. No. 4,357,240, Studer U.S. Pat. No. 3,936,373, Greenwald U.S. Pat. No. 4,067,443, Hennessey U.S. Pat. No. 4,288,316, Cerqueira U.S. Pat. No. 4,559,837, and Szabados U.S. Pat. No. 4,678,559. To facilitate the use of such collection and shipping vials, it is desirable to incorporate a screen and a collection device such as a scoop with the collection vial. However, it is critical to, at the same time, maintain a tight seal between any cap and the vial. Again, leakage during shipping is totally unacceptable.

One device that is particularly suitable to prevent leakage in storage is a device manufactured by Evergreen Scientific which incorporates a cap having a central collecting device or scoop. The cap has an outer wall and an inner wall, both of which engage the side wall of the collecting vial. However, this device provided for absolutely no filtration and basically incorporated a sampling device similar to that disclosed in the Grow patent or the Boettger patent. Accordingly, using a device such as this for filtration was apparently impossible.

It is also desirable to permit the end user easy access to the biological solution without requiring the laboratory technician to contact any biological fluid. Accordingly, it is preferable to incorporate, in addition to the sealed cap, the filtration and sample collecting device, an easy-access closure which acts to, in turn, prevent the laboratory technician from contacting the biological fluid.

SUMMARY OF THE INVENTION

The present invention is premised on the realization that a biological sample collecting and filtration device can be provided wherein the vial is closed with a cap having a large central opening and which has inner and outer annular walls, both of which engage the wall of the vial. A combination screen and sample collecting device is snap fitted to the bottom of the cap along the central opening and is totally separate from the collection vial. A push-pull nozzle or other easy-access nozzle is provided attached to the cap, separate from the screening device and sample collecting device. In the preferred embodiment, the screening device is simply snap fitted onto the cap.

In this manner, the cap can be unscrewed from the vial and sample collected and returned to the vial. The cap is securely screwed onto the vial. To remove liquid sample from the vial the easy-access opening is simply opened to allow material to go through the central opening of the cap by first passing through the screen. It then will exit the easy-opening nozzle, which can then be closed to prevent any leakage. In this manner, leakage of the biological sample is absolutely prevented, yet at the same time filtration is provided, easy access to the sample is provided, as well as a simple means for collecting the sample.

The objects and advantages of the present invention will be further appreciated in light of the following detailed description and drawing in which,

DETAILED DESCRIPTION

Figure 1:
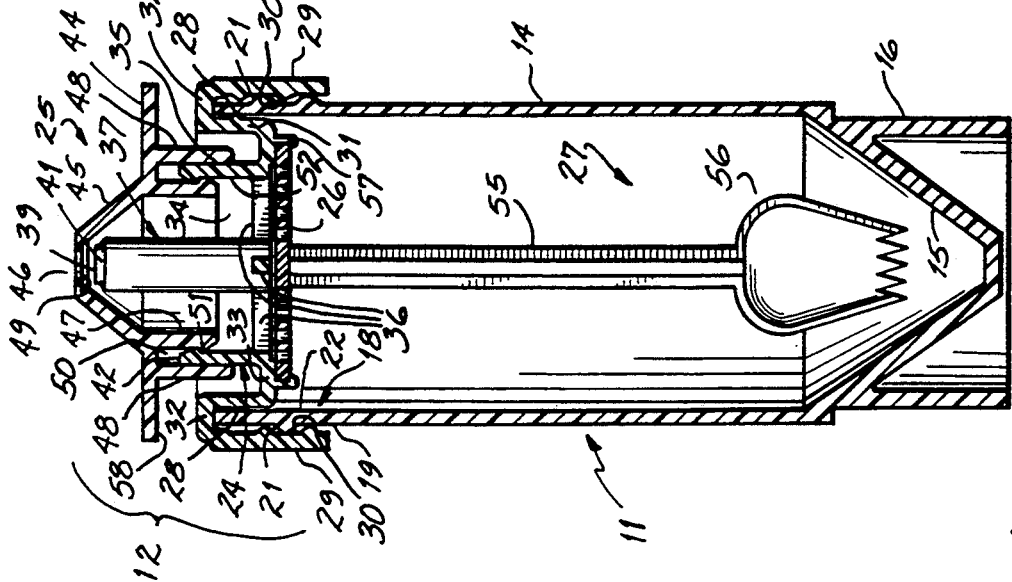
FIG. 1 is a cross-sectional view of the present invention shown in the open position.

As shown in FIG. 1, there is a sample collecting vial 11 secured with a cap 12. The via 11 includes a cylindrical side wall 14 having a tapered bottom 15 and a cylindrical base portion 16. Other configurations of the bottom of the vial can be used as necessary for the particular sample collection.

The upper portion 18 of vial 11 includes an external surface 19 having external threads 21 and an internal surface 22 opposite the external threads 21. The cap 12 is secured onto the upper portion 18 of the vial 11, as shown more particularly in FIG. 2. The cap 12 includes a central portion 24, a nozzle member 25 attached to the central portion, and a lower screen member 26 having a scoop 27 attached to the central portion thereof. The cap 12 includes two annular walls, an exterior annular wall 29 having internal threading 30, and an inner annular wall 31 connected by an annular ring portion 32. As shown, a bead 28 on wall 31 is designed to engage the internal surface 22 of vial 11.

The cap includes an enlarged upper central opening 34 which is defined by a third upper annular wall 35 which, in turn, is connected to the inner wall 31 of cap 12 by an annular base 33.

Figure 3:
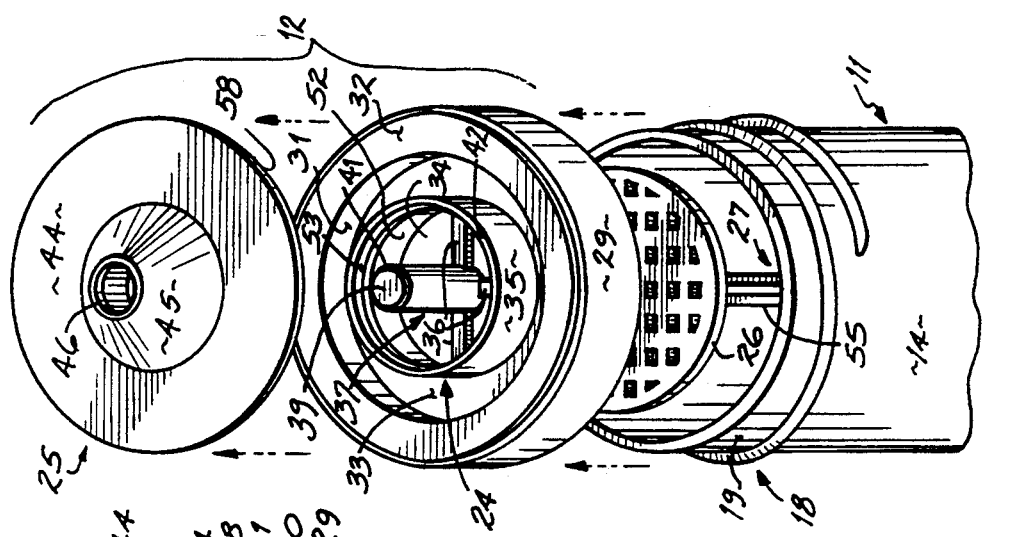
FIG. 3 is a disassembled perspective view of the present invention.

As best shown in FIG. 3, four prongs 36 extend from the base of wall 35 horizontally to a central portion of the central opening 34 and, in turn, support an axial post 37. Axial post 37 has a tip portion 41 which extends above the upper edge 42 of wall 35.

Covering the central opening 34 is the nozzle member 25. The nozzle member 25 includes an annular flange 44 and a frustoconnical tip 45 which includes a central opening 46 directly aligned with post 37. Extending axially downward from the annular flange are inner and outer walls 47 and 48, respectively, having an annular area 50 therebetween.

Wall 35 is held in this annular area 50 between walls 47 and 48. Inner wall 47 includes an outwardly extended bead or flange 51 which engages or rides along an inner surface 52 of wall 35. The rim 42 of wall 35 also includes an inwardly extended flange 53 adapted to engage flange 51 and prevent the nozzle member 25 from separating from the cap 12.

Figure 2:
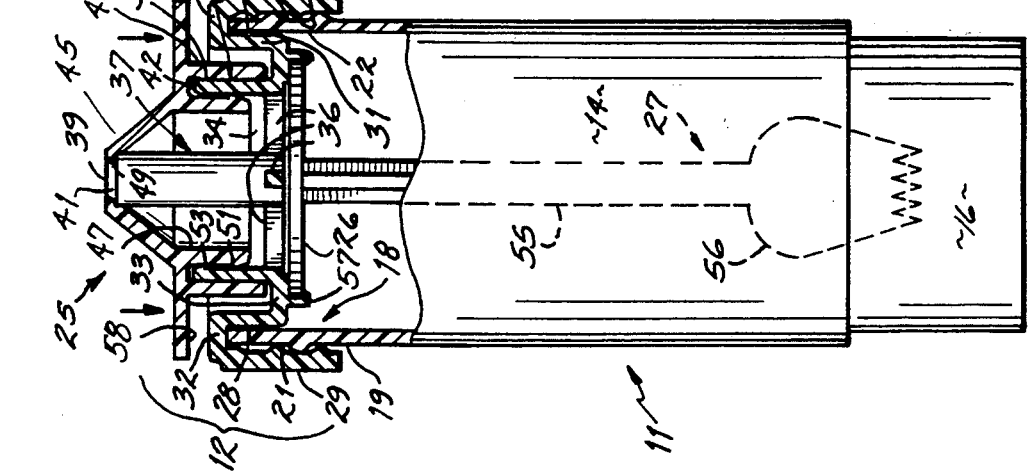
FIG. 2 is a cross-sectional view similar to FIG. 1 but in the closed position.

In this design, the nozzle member 25 can move axially relative to the cap, vial and post 37 from an open position, as shown in FIG. 1, to a closed position, shown in FIG. 2, where the nozzle member 25 is pushed against the cap and the upper edge 42 of wall 35 rests against the bottom surface 58 of annular flange 44. At the same time, the edge 49 which defines the central opening 46 will seat on the upper surface 39 of post 37. As shown, both have a corresponding stepped axial cross-sectional configuration which provides a seal when the nozzle member 43 is in the closed position.

Beneath the cap 12 is the screen disk 26 which blocks the central opening 34, permitting fluid from the vial to exit through the cap 12 only by passing through the holes in the filter disk 26.

Extended from the center of the screen disk is an arm 55 which has a scoop member 56 at the end opposite the screen disk 26. As shown, the screen disk 26 is snap-fitted onto the bottom of cap 12 by prongs 57.

In use, the entire cap 12 would be removed from vial 11 by unscrewing the cap 12 from the vial 11. A sample would be collected using scoop 27 and placed inside the vial, which would preferably include a liquid medium for use in testing or preserving the biological sample. The cap 12 would then be tightly screwed onto the vial 11 and the nozzle member 25 closed so that edge 49 of nozzle 25 would seat on the edge 41 of post 37. This would then be taken to a testing laboratory.

The testing laboratory would simply pull flange 44, opening the nozzle 25 by separating edge 49 from edge 41 of post 37. Liquid sample would then be removed by simply inverting the vial, allowing liquid to flow through the screen disk 26 through the central opening 34 and through hole 46. Once a sufficient amount of sample is removed, the nozzle member 25 would be pressed downwardly, again providing a seal.

As shown, the particular cap 12 provides for the inner and outer wall to engage an inner and outer surface of the vial 11. This provides a particularly tight seal, preventing any leakage. At the same time, the screening and collection device is connected to the cap providing greater flexibility and improving the ease of use. Further, the cap is provided with an easy push-pull nozzle which allows the laboratory technician to easily access the liquid biological sample and minimizes any contact with the biological sample. Thus, the present invention provides an all-in-one sample collection, shipping and testing vial.

Although this has been a description of the present invention and the preferred embodiment currently known to the inventor, the invention itself should be defined only by the appended claims wherein we claim:

1. A sample holding device comprising a vial and a cap;
   said cap sealingly fastenable to said vial;
   said cap having a top portion, including a peripheral means to attach to said vial, and a first central opening of said cap;
   wherein said top portion of said cap includes a post held in said first central opening and extending above said first central opening;
   a nozzle member having a second central opening, said nozzle member axially movable relative to said post from an open position where said second central opening is spaced from said post to a closed position whereby said second central opening is blocked by an upper portion of said post,
   a screen fixed to said cap inwardly and separate from said sealing means, said screen covering said first central opening,
   and wherein said screen is a rigid disk attached to a bottom side of said cap, and wherein said screen includes a sample collecting arm extending away from said first central opening.

2. A sample collecting device claimed in claim 1 wherein said top portion of said cap has internal threads adapted to engage external threads on an outside wall of said vial, said top portion further having an inner annular wall adapted to engage an inside wall of said vial opposite the external threading and wherein said screen is attached to said inner annular wall separate from said vial.

3. A sample collecting device claimed in claim 2 wherein said cap has an upwardly-extended annular wall surrounding said first central opening and a flange, and wherein said nozzle member has an annular wall complementary with said annular wall of said cap and also includes a lip engagable with a lip of said annular wall surrounding said first central opening, wherein said lips engage each other preventing said nozzle member from completely separating from said cap.

4. A sample holding device comprising a vial and a cap, said cap sealingly fastenable to said vial and including an external wall having internal threads adapted to engage external threads along a top portion of said vial;
   said cap further including an internal annular wall engagable with an internal surface of said vial opposite the external threading and defining a first central opening through said cap, said cap further including an upwardly extended annular wall surrounding said first central opening and having a lip and a post extended through said first central opening above said annular wall;
   a nozzle member having an annular wall surrounding and engagable with the upper annular wall of said cap, slidable axially relative to said post, said nozzle member further having a second central opening engagable with a top portion of said post when said nozzle member is in a closed position;
   an annular screen attached to a bottom portion of said cap covering said first central opening, said screen having a sample collecting arm extending downwardly away from said post, said screen remaining separate and spaced from said vial and connected only to said cap portion.

* * * * *